United States Patent [19]

McGinnis et al.

[11] 4,374,262

[45] Feb. 15, 1983

[54] PREPARATION OF HYDROXY AROMATIC CARBOXYLIC ACIDS AND ESTER DERIVATIVES THEREOF

[75] Inventors: James L. McGinnis, Middlesex; Anthony B. Conciatori, Chatham, both of N.J.

[73] Assignee: Celanese Corporation, New York, N.Y.

[21] Appl. No.: 194,201

[22] Filed: Oct. 6, 1980

[51] Int. Cl.$^3$ .............................................. C07C 69/94
[52] U.S. Cl. ..................................... 560/56; 562/406; 562/467; 562/475; 568/737; 568/774; 568/779; 560/67
[58] Field of Search ............................ 560/56, 64, 67; 562/406, 467, 475

[56] References Cited

U.S. PATENT DOCUMENTS 3,700,729 10/1972 Fenton ................................ 562/406
3,717,670 2/1973 Schultz ............................... 562/406

OTHER PUBLICATIONS

Falbe, J., "Carbon Monoxide in Organic Synthesis", pp. 118–120, Springer–Verlag, 1970.

*Primary Examiner*—Paul J. Killos
*Attorney, Agent, or Firm*—Burns, Doane, Swecker & Mathis

[57] ABSTRACT

A process for preparing hydroxy aromatic carboxylic acids, or the ester derivatives thereof, comprises carbonylating a hydroxy aromatic halide in the presence of a reactive alcohol solvent and a catalytic amount of a Group VIII metal catalyst. The process has particular applicability to the preparation of 6-hydroxy-2-naphthoic acid from 6-bromo-2-naphthol, which can be easily prepared from β-naphthol, a readily available and inexpensive starting material.

27 Claims, No Drawings

PREPARATION OF HYDROXY AROMATIC CARBOXYLIC ACIDS AND ESTER DERIVATIVES THEREOF

BACKGROUND OF THE INVENTION

1. Field of the Invention

This invention relates to a novel process for preparing hydroxy aromatic carboxylic acids or the corresponding ester derivatives thereof. More particularly, this invention relates to a novel process for the preparation of hydroxy aromatic carboxylic acids such as 6-hydroxy-2-naphthoic acid by the carbonylation of a hydroxy aromatic halide.

2. Description of the Prior Art

Hydroxy aromatic carboxylic acids and their application in various technological areas such as dyes and pigments are well known in the art. The technological applications of hydroxy aromatic acids are also continuing to expand. An example of one hydroxy carboxylic acid in particular whose technological applicability has resulted in an increased demand for the compound is 6-hydroxy-2-naphthoic acid. The increased demand for such hydroxy aromatic acids has also intensified the search for more commercially acceptable methods of synthesizing said compounds.

The formation of aromatic carboxylic acids or functional derivatives thereof by reactions involving the carbonylation of aromatic systems is well recognized in the art. One type of reaction between an aromatic system and carbon monoxide involves the insertion of a carbonyl group into a molecule between the aromatic moiety and a functional moiety attached thereto. For example, U.S. Pat. No. 3,452,090 discloses a process for the production of aroyl halides in which an aryl halide is reacted with carbon monoxide in the presence of a platinum, palladium, ruthenium, rhodium, osmium, or iridium catalyst and an inert solvent. The reaction takes place at the site of the halogen resulting in the insertion of a carboxyl group into the molecule to thus form the aroyl halide. The aforegoing patent discloses that substituents other than the halogen groups can be attached to the aromatic system as long as the substituents are inert and are not affected by the reaction. Examples of such inert substituents are the alkyl groups and nitro groups. Hydroxy groups are not disclosed, however, as possible substituents.

A. Schoenberg et al, in the *Journal of Organic Chemistry*, Volume 39, pp. 3318-3326 (1974), disclose the reaction of aryl and vinylic bromides and iodides with carbon monoxide and an alcohol in the presence of a tertiary amine and a catalytic amount of a palladium-triphenylphosphine complex to form esters. With respect to substituent effects, the carbonylation was reported to proceed most rapidly with electron withdrawing substituents on the aromatic ring, in contradistinction to electron donating substituents which produced appreciably decreased reaction rates. As well, the brominated naphthalenes were reported as being significantly less reactive than other aryl bromides. Based upon said reports the carbonylation of a hydroxy aromatic halide, and in particular a brominated naphthol, to obtain a hydroxy aromatic acid such as 6-hydroxy-2-naphthoic acid, or the corresponding ester thereof, would appear to have little chance, if any, of success. Indeed, no attempt to carbonylate a hydroxy aryl bromide or iodide was reported.

Stille, et al, in the *Journal of Organic Chemistry*, Volume 40, pp. 532-534 (1975), and Hidai et al, in the *Bulletin of the Chemical Society of Japan*, Volume 48, pp. 2075-2077 (1977), disclose the reaction of organic halides in the presence of an alcohol and palladium complex catalyst. However, the reaction of hydroxy organic halides is not reported.

U.S. Pat. Nos. 3,769,324 and 3,769,326 disclose the carbonylation of hydroxy aromatic compounds. However, the carbonylation reaction takes place at the site of the hydroxy group. More specifically, carboxylic acids and their esters can be obtained by reacting aromatic alcohols, and the ester, ether, and halide derivatives thereof, with carbon monoxide in the presence of an iridium, osmium or ruthenium catalyst system. The reaction can take place under a broad range of temperature and pressure conditions, e.g., a temperature in the range of 50°-300° C. and a carbon monoxide partial pressure in the range of 1-15,000 psi, with the reaction involving the insertion of a carbonyl between the hydroxy, ester, ether or halide moiety and the remainder of the molecule. For example, benzoic acid is prepared from a phenol feedstock and phenyl acetic acid from a benzyl alcohol feedstock.

U.S. Pat. No. 2,565,463 discloses a process for the carbonylation of organic halides wherein an aryl halide is reacted with carbon monoxide in the presence of a carboxylic acid modifier, e.g., an alkanoic acid such as acetic, propionic, succinic, adipic, stearic or palmitic acid. The presence of the carboxylic acid modifier results in the formation of an anhydride product which can then be readily converted to the acid upon the subsequent addition of water.

U.S. Pat. No. 3,009,951 discloses a process for carbonylating an aryl halide to produce carboxylic acids or their corresponding esters and salts. The ester of an aromatic carboxylic acid is obtained upon conducting the reaction in the presence of an alcohol.

U.S. Pat. No. 4,016,194 discloses the preparation of phenylenediacetate diesters by the catalytic insertion of carbon monoxide into the carbon-chlorine bonds of α,α'-dichloroxylenes by the reaction of said xylenes in the presence of alcohols.

Two-phase reaction mediums have also been employed successfully in preparing carboxylic acids via the carbonylation of an aromatic system. For example, U.S. Pat. No. 3,034,004, discloses the reaction of an organic halide with carbon monoxide with said reaction being conducted in an organic/aqueous biphase system.

U.S. Pat. No. 3,700,729, discloses reacting an organic aromatic compound, which can be a phenol or naphthol, with carbon monoxide in the presence of a substantially anhydrous organic liquid reaction medium which contains a catalyst and is inert to said reactants and catalyst. However, the reaction proceeds purely as an oxidation reaction to thus produce an oxidatively carbonylated aromatic compound which can be subsequently hydrolyzed to form the aromatic acid. No insertion of CO per se is involved.

Although the prior art has recognized, as evidenced by the aforementioned patents, many different processes involving various reactants, reaction media, catalysts and reaction parameters for the formation of aromatic carboxylic acids by carbonylated an aromatic system with insertion of a carbonyl group, such a reaction has not been employed to produce hydroxy aromatic carboxylic acids, and more particularly, hydroxy naphthoic acids. Instead, hydroxy aromatic carboxylic acids such as the naphthoic acids, and in particular, 6-hydroxy-2-naphthoic acid, have typically been prepared by other methods. These methods, however, due to the disadvantages associated with each, has limited the commercial application of hydroxy aromatic carboxylic acids.

For instance, one of the first reactions to form the specific hydroxy aromatic carboxylic acid, 6-hydroxy-2-naphthoic acid, was reported in 1923 by Butler and Royle in the *Journal of the Chemical Society*, Volume 123, p. 1649. The synthesis involved initially producing 2-cyano-6-naphthalene sulfonic acid by diazotizing Bronners' Acid (2-amino-6-naphthalene sulfonic acid) with sodium nitrite in the presence of hydrochloric acid and then treating with cuprous cyanide in accordance with the well known Sandmeyer Reaction. The 2-cyano-6-naphthalene sulfonic acid is then hydrolyzed with potassium hydroxide to the potassium salt of 2-carboxy-6-naphthalene sulfonic acid, which is then fused with potassium hydroxide at 260°–280° C., or treated with a 25% aqueous solution of potassium hydroxide at 260° C. in 30 atmospheres of pressure, to thereby produce the 6-hydroxy-2-naphthoic acid. The overall yield from the initial starting material of Bronners' Acid is about 50%, which is an attractive reaction yield for commercialization purposes. One of the disadvantages associated with the Butler et al synthesis stems from the fact that Bronners' Acid is a carcinogen and/or generally contains the potent carcinogen β-naphthyl amine as an impurity. Moreover, hydrogen cyanide is evolved during the Sandmeyer Reaction. Thus, to commercialize the aforegoing process would be extremely costly due to the necessary provision of safeguards for the handling of the Bronners' Acid and the protection of the workers against the hydrogen cyanide evolution.

Another process for forming 6-hydroxy-2-naphthoic acid is a two step synthesis route discussed by Cason in the *Journal of the American Chemical Society*, Volume 63, page 828 (1941). In the first step of this process, potassium cyanide or potassium ferricyanide is fused with Bronners' Acid in order to replace the sulfonic acid grouping with a cyano group. The second step involves a hydrolysis of the cyano group with simultaneous replacement of the amino group with hydroxyl to thereby form the 6-hydroxy-2-naphthoic acid. Unfortunately, the yield of the 6-hydroxy-2-naphthoic acid is extremely low, which, along with the disadvantages inherent in the handling of the carbinogenic Bronners' Acid and the possibility of hydrogen cyanide evolution during the potassium cyanide or potassium ferricyanide fusion step, make the process extremely unattractive for commercial purposes.

Knowles et al reports another process for synthesizing 6-hydroxy-2-naphthoic acid in the *Journal of Organic Chemistry*, Volume 1, page 374 (1942). The hydroxy carboxylic acid is prepared from a starting material of 6-methoxy-2-bromonaphthalene, which is prepared from β-naphthol in three steps. Once the 6-methoxy-2-bromonaphthalene is obtained, its Grignard reagent is prepared and then carbonated to provide a 50% yield of 6-methoxy-2-naphthoic acid. The 6-hydroxy-2-naphthoic acid is then obtained from the methoxy compound by cleaving the methylether with hydrobromic acid (HBr) in aqueous acetic acid. The yield of 6-hydroxy-2-naphthoic acid is about 75%.

A process for preparing 6-hydroxy-2-naphthoic acid from 6-methoxy-2-bromonaphthalene differing from that reported by Knowles et al was subsequently reported in the *Journal of the American Chemical Society*, Volume 65, page 234 (1943) by Anderson et al. This synthesis involves acetylating the 6-methoxy-2-bromonaphthalene in nitrobenzene with acetyl chloride in the presence of aluminum chloride to give a 50% yield of 6-methoxy-2-acetonaphthone. The acetonaphthone is then oxidized with hypobronite (NaBrO) to give a 75% yield of 6-methoxy-2-naphthoic acid, which is then demethylated with hydrobromic acid in aqueous acetic acid to produce the 6-hydroxy-2-naphthoic acid.

The Knowles et al and Anderson et al syntheses have met with limited commercial acceptance, however, due to the undesireable use of the cancer suspect agents, dimethyl sulfate and nitrobenzene, as well as the large number of reaction steps, i.e., beginning initially with a three step process to initially produce the 6-methoxy-2-bromonaphthalene and then subsequently obtaining the 6-hydroxy-2-naphthoic acid by an additional two or three steps.

Another well known procedure for synthesizing the 6-hydroxy-2-naphthoic acid is via the Kolbe-Schmidt reaction (see U.S. Pat. No. 257,815; cf. U.S. Pat. No. 1,593,816). This process involves the reaction of potassium naphtholate with carbon dioxide in the absence of a solvent at a temperature in the range of about 170°–230° C. for about eight hours. The product obtained is a mixture of 6-hydroxy-2-naphthoic acid and 3-hydroxy-2-naphthoic acid. It has been reported that the 6-hydroxy-2-naphthoic acid can be recovered with 28–36% yield; however, other experimental reports, such as that by E. Schwenk in *Chemiker-Zeitung*, Nr. 30, S297-304, (1929) and Nr. 34, S333-340 (1929), have indicated problems in obtaining the 6-hydroxy-2-naphthoic acid in the aforegoing yields via the Kolbe-Schmidt reaction.

Thus, the search has continued for a more commercially advantageous process for the production of hydroxy aromatic carboxylic acids in general, and more specifically, 6-hydroxy-2-naphthoic acid. Such a process would most desirably overcome the problems of the prior art processes, i.e., avoiding the handling of carcinogens or the production of toxic materials, employing a limited number of steps and consistently producing the desired product in a good yield. The instant invention was developed in response to this search.

Accordingly, it is an object of this invention to provide a novel process for producing hydroxy aromatic carboxylic acids via carbonylation.

Another object of this invention is to provide a process for producing hydroxy aromatic carboxylic acids wherein the handling of carcinogens is substantially avoided.

Another object of this invention is to provide a process for producing hydroxy aromatic carboxylic acids in good yields.

Another object of this invention is to provide a commercially viable and economically acceptable process for the production of hydroxy aromatic carboxylic acids wherein inexpensive starting materials are employed and a large number of reaction steps is avoided.

Another object of the present invention is to achieve regioselectivity in the synthesis of hydroxy aromatic acids.

These and other objects, as well as the scope, nature and utilization of the invention, will be apparent to those skilled in the art from the following description and the appended claims.

SUMMARY OF THE INVENTION

It has not been unexpectedly and most surprisingly discovered that hydroxy aromatic carboxylic acids, or the ester derivative thereof, can be prepared in good yields by reacting a hydroxy aromatic halide with carbon monoxide under carbonylation reaction conditions in the presence of a catalytically effective amount of a Group VIII catalyst and, most critically, a reactive alcohol solvent. It has been found that reaction in the presence of a reactive alcohol solvent enhances the carbonylation reaction and thus allows the desired product to be obtained in good yields despite the adverse presence of the reactive, electron-donating hydroxy substituent, which otherwise interferes with such reactions. The reactive alcohol solvent generally contains from one to about eight carbon atoms, and is preferably a straight chain alkanol.

In accordance with another embodiment of this invention, 6-hydroxy-2-naphthoic acid, or the corresponding ester, is produced from a relatively inexpensive and readily available starting material, β-naphthol, in a relatively minimal number of reaction steps. This particular aspect of the invention comprises the reaction of β-naphthol with bromine under bromination reaction conditions sufficient to produce 1,6-dibromo-2-naphthol. The 1,6-dibromo-2-naphthol is then reacted with hydrobromic acid in the presence of metallic tin to produce a hydroxy aromatic halide, i.e., 6-bromo-2-naphthol. Said hydroxy aromatic halide is then carbonylated with carbon monoxide under carbonylation reaction conditions as described above in the presence of a reactive alcohol solvent and a catalytic amount of a Group VIII metal catalyst to produce the 6-hydroxy-2-naphthoate. Hydrolysis of the 6-hydroxy-2-naphthoate will then produce 6-hydroxy-2-naphthoic acid. In a further embodiment thereof, the hydroxy aromatic halide, i.e., 6-bromo-2-naphthol, can be acetylated prior to carbonylation.

DESCRIPTION OF THE PREFERRED EMBODIMENTS

The process of the instant invention provides one with a relatively safe and economically attractive process for preparing hydroxy aromatic carboxylic acids or their alkyl esters in good yields. The instant invention is comprised of two general embodiments, namely, (1) carbonylating a hydroxy aromatic halide in the presence of a reactive alcohol solvent and a catalytic amount of a Group VIII metal catalyst; and (2) preparing 6-hydroxy-2-naphthoic acid from β-naphthol by converting the β-naphthol to 6-bromo-2-naphthol and then carbonylating the 6-bromo-2-naphthol in the presence of a reactive alcohol solvent and a Group VIII metal catalyst.

The first embodiment of the instant invention can be illustrated by the following scheme, which pertains to the preparation of the methyl ester of 6-hydroxy-2-naphthoic acid by carbonylating 6-bromo-2-naphthol in the presence of a palladium catalyst and methanol as the reactive alcohol solvent:

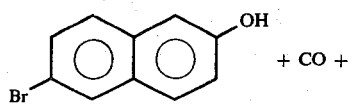
+ CO +

-continued
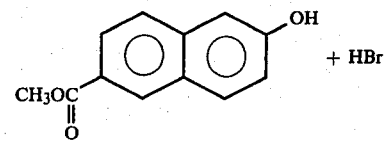
+ HBr

As is self-evident from the above schematic, acid is formed during the carbonylation reaction upon the elimination of the halide from the aromatic system by the alcohol to form the ester product. In the above schematic the acid formed is hydrobromic acid. If the halogen substituent is chloride, iodine, or fluorine, however, hydrochloric, hydriodic, or hydrofluoric acid would be formed respectively. In order to neutralize said acid formed during the reaction, a small amount of a weak base can be added to the reaction medium. Any weak base known to the prior art which does not interfere with the reaction can be employed. Representative examples of suitable weak bases include the amines, such as triethylamine, diethylamine, trimethylamine or tri-n-propylamine, with the tertiary amines being most preferred. Generally, an amount of weak base sufficient to provide neutralization of all acid formed is added.

Once the reaction is completed, i.e., upon completion of the absorption of carbon monoxide, the product can be recovered from the reaction medium using conventional separation and recovery techniques well known to the art, such as filtration, recrystallization, extraction, distillation, sublimation, or chromatography. For example, methyl 6-hydroxy-2-napthoate, obtained via the carbonylation of 6-bromo-2-naphthol in accordance with the present invention, can be recovered by filtering off the solid residues, rinsing the filtrate with water, evaporation of the solvent, and crystallization of the product from an organic solvent such as benzene, ether/petroleum ether, or ethyl acetate.

It is critical that the carbonylation reaction of the hydroxy aromatic halide in accordance with the instant invention take place in a reactive alcohol solvent. The term reactive alcohol solvent as used herein means an alcohol solvent which reacts during the carbonylation reaction only through its hydroxy functional group. It has been surprisingly discovered that reaction in a reactive alcohol solvent results in good yields, in contradistinction to the yields obtained by the use of inert organic solvents, water, or biphase reaction mediums employing both an organic solvent and water. Mixed solvents, i.e., comprising an alcohol and an inert solvent, are also appropriate as long as the mixture contains a molar excess of alcohol.

Reaction in the presence of a reactive alcohol solvent is believed to overcome the detrimental effect of the hydroxy substituent of the aromatic halide which would otherwise be expected to interfere with the reaction by reacting with itself to form an undesirable product, e.g., a polymer, and thus result in yields of the desired product of about 1% or less. Reaction in the presence of an alcohol solvent, however, surprisingly allows the reaction to proceed to the desired product (the ester of a hydroxy aromatic carboxylic acid) in yields of greater than 30%, even when the hydroxy is a substituent of a naphthalene system. This is particularly surprising in light of recent reports that carbonylations of aromatic bromides are favored with election withdrawing substituents on the aromatic ring in contradistinction to the inhibiting effects of electron donating substituents; and, furthermore, that naphthalene derivatives are significantly less reactive than other aromatics. [A. Schoenberg et al, *Journal of Organic Chemistry*, Volume 39, pp. 3318–3326, (1974)]. Since a hydroxy is an electron donating substituent, these two effects would further project complete inhibition of a carbonylation reaction of a halogenated naphthol such as 6-bromo-2-naphthol, yet, good yields have been obtained via the process of the present invention.

Although conducting the reaction in the presence of a reactive alcohol solvent results in the formation of an ester product, if desired, said ester can be hydrolyzed to the acid quite easily by techniques known to the art, for example, by the addition of acid. In many cases, however, the ester derivative may be the preferred form of the product, depending, of course, on its ultimate use.

The preferred reactive alcohol solvent is a monohydric primary, secondary, or tertiary alkanol having from about 1 to about 8, preferably from about 1 to about 4, carbon atoms. Straight chain or primary alcohols are most preferred. Suitable examples include methanol, ethanol, isopropanol, 1-hexanol, 2-pentanol, 1-butanol, 3-butanol, 2-ethylhexanol and t-butanol. Methanol is the most preferred alcohol solvent.

Generally, the amount of alcohol employed as the reactive solvent is preferably at least sufficient to dissolve the reactants and satisfy the stoichiometry of the reaction, with an excess amount being of no adverse consequence. Thus, although any effective amount of reactive solvent may be employed, it is preferred that the weight ratio of solvent employed to hydroxy aromatic halide be in the range of about 0.5 to about 100, more preferably from about 1 to about 10, and most preferably from about 3 to about 8.

Although the above schematic illustrating the first embodiment of the instant invention employs 6-bromo-2-naphthol as the hydroxy aromatic halide, the invention is not limited thereto. For the purposes of this invention, the hydroxy aromatic halide can be any mono- or poly-cyclic aromatic compound containing a hydroxy ring substituent and at least one, preferably one, halogen ring substituent. The hydroxy aromatic halide can also contain other ring substituents which are inert to the reactants, catalyst, and solvent, and are stable under the reaction conditions. Examples thereof are the alkyl substituents.

Examples of other suitable hydroxy aromatic halides are the halogenated phenols such as ortho-, meta-, or parachloro phenol; ortho-, meta-, or para-bromo phenol; ortho-, meta- or para-iodo phenol; the halogenated naphthols such as 1-chloro-2-naphthol, 1-bromo-2-naphthol, 1-iodo-2-naphthol, 4-chloro-2-naphthol, 4-bromo-2-naphthol, 4-iodo-2-naphthol, 5-chloro-2-naphthol, 5-bromo-2-naphthol, 6-chloro-2-naphthol, 6-iodo-2-naphthol, 7-bromo-2-naphthol, 8-bromo-2-naphthol, 5-bromo-1-naphthol, 6-iodo-1-naphthol, 6-bromo-1-naphthol, and the like; halogenated and hydroxylated anthracenes such as 1-chloroanthranol, 4-chloro-2-hydroxyanthracene. 5-chloro-2-hydroxyanthracene, 6-chloro-2-hydroxyanthracene, 4-bromo-2-hydroxyanthracene, 5bromo-2-hydroxyanthracene, 6-bromo-2-hydroxyanthracene, and the like; alkyl substituted hydroxy aromatic halides, e.g., 4-bromo-2-methyl phenol, 4-chloro-2-methyl phenol, 6-bromo-1-methyl-2-naphthol, 5-bromo-1-methyl-2-naphthol, 6-bromo-3-methyl-2-naphthol, and the like; and, dihalo hydroxy aromatic halides such as 2,4-dichloro phenol, 1,6-dichloro-2-naphthol, 1,6-dibromo-naphthol, and the like.

The preferred hydroxy aromatic halides to which the process of the invention has application, however, are the halogenated phenols and naphthols, particularly the naphthols, and most particularly the brominated and iodinated naphthols as the bromine and iodine ring substituents are generally more reactive than those of the other halogens. The most preferred hydroxy aromatic halide reactant is 6-bromo-2-naphthol as carbonylation thereof in accordance with the instant invention will allow one to obtain the commercially desirable 6-hydroxy-2-naphthoic acid is good yields.

In another embodiment of this invention, there is provided a low-cost process for preparing the commercially desirable 6-hydroxy-2-naphthoic acid from a relatively inexpensive starting material, namely, β-naphthol. This ability to prepare 6-hydroxy-2-naphthoic acid from an initial low-cost starting material such as β-naphthol in a minimal amount of steps is a major advantage of the instant invention. The route from β-naphthol, which is commercially available and relatively inexpensive, is plausible due to the surprising discovery that the hydroxy aromatic halide 6-bromo-2-naphthol can be carbonylated effectively in accordance with the instant invention to produce the hydroxy aromatic carboxylic acid, 6-hydroxy-2-naphthoic acid, in good yields. The reaction-steps can be illustrated by the following schematic:

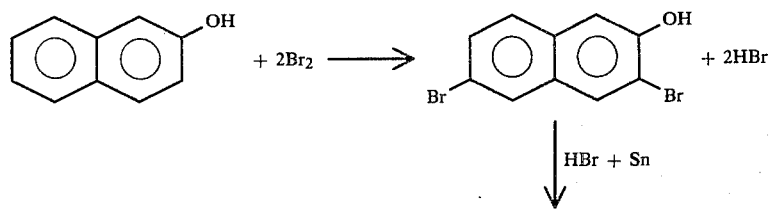

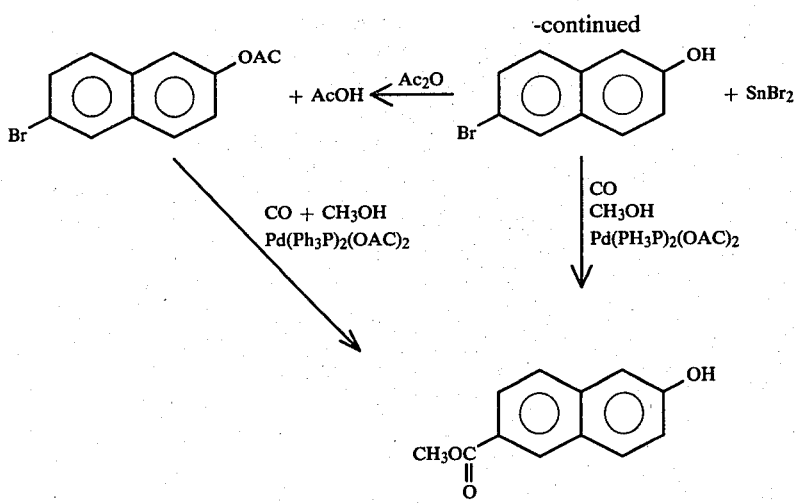

The first step of the process is converting the β-naphthol to 6-bromo-2-naphthol. This can be achieved by reacting the β-naphthol with bromine in the presence of an organic solvent such as glacial acetic acid. During the reaction, hydrogen bromide is evolved. Metallic tin, e.g. mossy tin, is then added to the system of 3,6-dibromo-2-naphthol and hydrogen bromide to produce a product of 6-bromo-2-naphthol. The 6-bromo-2-naphthol can then be recovered using conventional techniques in a yield of 96–100%. This procedure is known in the art and is reported by C. Frederick Koelsch in *Organic Syntheses, Collective Volume* 3, E. C. Horning (ed.), John Wiley and Sons, New York, 1955, pp. 132–133. Although this is the preferred process for preparing 6-bromo-2-naphthol from β-naphthol due to its high yield, other processes known in the art, e.g., bromination of 2-naphthol with pyridinium bromide perbromide can also be employed if desired.

Once the 6-bromo-2-naphthol has been prepared, it can be carbonylated with carbon monoxide under carbonylation conditions in the presence of a catalytic amount of a Group VIII metal catalyst and a reactive alcohol solvent. In a further embodiment, said 6-bromo-2-naphthol can be first acetylated and then carbonylated to form the ester, 2-hydroxy-6-naphthoate. In actuality, the hydroxy group can be converted to any ester group, however, for practical purposes, conversion to the acetate is preferred via acetylation. Any acetylation procedure known to the art can be employed. For example, the 6-bromo-2-naphthol can be reacted with the well known acetylation agents acetic anhydride or acetyl chloride to form the corresponding acetoxy compound. Said acetoxy is then carbonylated in the same manner as the hydroxy aromatic halide, 6-bromo-2-naphthol, to yield the hydroxy naphthoate. The isolated product is not acetylated as the reaction conditions are apparently sufficient to cause transesterification of the alcohol solvent and of the acetylated 6-bromo-2-naphthol and/or 2-hydroxy-6-naphthoate.

The carbonylation of the hydroxy aromatic halide in accordance with the instant invention is conducted in the presence of a catalytic amount of a Group VIII metal catalyst. Any Group VIII catalyst known to the art as being catalytically active for carbonylation reactions, such as those disclosed in U.S. Pat. Nos. 3,452,090, 4,016,194, and 4,034,004, and the publication by A. Schoenberg, I. Bartoletti, and R. F. Heck in *Journal of Organic Chemistry*, Volume 39, pp. 3318–3326(1974), the disclosures of which are herein expressly incorporated by reference, can be employed in the process of the instant invention. It is preferred, however, that the catalyst be selected from the palladium and platinum subgroups, i.e., from the group consisting of palladium, platinum, ruthenium, rhodium, osmium and iridium catalysts. The catalyst can be employed in the form of a salt, such as the chloride, bromide, fluoride, iodide, nitrate, sulfate or acetate; as the oxide; as the complex of the metal with an inorganic or organic complexing or chelate-forming compound, such as the phosphines, the benzonitrile, the acetylacetonate, or the bis-π-aryl complex; or in the form of the metal, salt, oxide or complex supported on an inert carrier, for example, carbon, alumina, or silica.

Examples of suitable catalysts are: palladous chloride and palladous bromide; palladium on carbon; palladous nitrate; palladous benzoate; platinous oxide; bis(benzonitrile) palladous chloride; the chlorides and bromides of rhodium, ruthenium, platinum, iridium, and osmium; platinous acetate; rhodium oxide; ruthenium carbonate; potassium chloropalladite; palladous acetyl acetonate, and phosphinic palladium complexes such as bis(triphenyl phosphine) palladous acetate and bis(triphenyl phosphine) palladous chloride.

Compounds known to complex with the platinum-palladium group metals can also be added in excess amounts so that free liquids are present as co-catalysts, or in addition to said platinum or palladium subgroup metal catalyst so that the ligand is present purely as a co-catalyst. Examples of such ligands include triphenyl phosphine, pyridine, benzonitrile, and pentane-1,3-dione.

Palladium catalysts are readily available, relatively inexpensive and give excellent results, therefore, palladium catalysts are preferred.

The most preferred palladium catalyst is a palladium complex with phosphines selected from among:
(i) at least one zero-valent palladium complex with $P(R)_3$, i.e., a phosphine of the formula $Pd[P(R)_3]_m$ wherein m is a whole number from 2 to 4 and $(R)_3$ represents a homogenous or heterogeneous group consisting of phenyl and/or alkyl radicals which, if desired, may preferably be substituted phenyl groups;
(ii) at least one zero-valent palladium complex of the general formula $Pd[(R)_3P\text{-}(CH_2)_n\text{-}P(R)_2]_p$ wherein (R)₂ has the same meaning as indicated above for (R)₃,p is a whole number from 1 to 2, and n is a whole number from 1 to 6, or;

(iii) at least one palladium complex of the general formula:

wherein the groups (R)₃, equal to or different from each other, have the same meaning as indicated above and where Y is a halogen atom and/or an acetate.

The phosphine palladium complex can be directly added to the reaction medium or obtained by insitu reaction via techniques well known to the prior art. The most preferred phosphinic palladium complex catalyst, due to the availability and inexpensiveness of the phosphine, is that of a palladium triphenyl-phosphine, e.g., bis(triphenyl phosphine) palladous acetate.

An effective amount of catalyst is employed with very small amounts being effective to bring about the reaction. In general, about 0.001 to about 20 mole percent, based upon the amount of hydroxy aromatic halide employed, can be used. The preferred proportion is within the range from about 0.01 to about 10 mole percent. Two or more catalysts can be employed in admixture, if desired, with advantageous effect.

When a ligand is employed as a co-catalyst, small amounts of such co-catalysts suffice. Amounts within the range from about 10 to about 500 mole percent based on the catalyst are usually adequate, although more or less can be used without adverse effect.

The reaction conditions under which the hydroxy aromatic halide is carbonylated for purposes of this invention are those generally employed for carbonylation reactions and which are well known to the prior art, e.g., those disclosed in U.S. Pat. Nos. 3,452,090 and 4,016,194, or the article by A. Schoenberg et al, *Journal of Organic Chemistry,* Volume 39, pp. 3318–3326 (1974). Thus, the reaction can be run employing conventional carbonylation reaction conditions sufficient to produce the hydroxy aromatic carboxylic acid or its corresponding ester.

The temperature employed can be any effective temperature, but it is preferred that the temperatures employed are generally in the range from about 20° C. to about 250° C., more preferably from about 75° C. to about 200° C., and most preferably in the range from about 90° C. to about 110° C. The pressure under which the reaction is run is generally in the range from about atmospheric to about 2000 psig, preferably from about 100 to 1500 psig, and most preferably from about 300 to 1000 psig.

The reaction is run under an atmosphere of carbon monoxide, which can be bubbled through the reaction mixture if desired. The carbon monoxide atmosphere can be purely carbon monoxide or can contain one or more inert gases such as nitrogen, argon, neon and the like. It is preferred, however, that the inert substituents are present in less than a majority amount, i.e., less than 50% by volume. The amount of carbon monoxide supplied, however, should be sufficient to that at least a stoichiometric amount of carbon monoxide is present for the reaction, i.e, at least one mole of carbon monoxide per mole of halogen substituents at which site carbonylation can occur. An excess of carbon monoxide over the aforesaid stoichiometric amount can be present.

The time for the reaction to run to completion will vary depending on the temperature conditions employed, the concentration of the reactants and catalyst, and the particular reactants and catalyst employed. Generally, however, the reaction is completed in about 2 to about 100 hours.

Any suitable reactor for holding a gaseous atmosphere, e.g., an autoclave, can be employed as the particular type is not critical. The size of the reactor used will vary depending upon the volume of reactants one wishes to subject to the reaction conditions. Constant agitation, e.g., stirring, of the reaction medium is generally employed to provide for appropriate mixing of the CO gas and liquid reaction medium.

The following examples are given as specific illustrations of the claimed invention. It should be understood, however, that the specific details set forth in the examples are merely illustrative and in nowise limitative. All parts and percentages in the examples and the remainder of the specification are by weight unless otherwise specified.

EXAMPLE 1

Example 1 exemplifies a procedure for preparing 6-bromo-2-naphthol from β-naphthol.

In a 3 l. round-bottomed flask fitted with a dropping funnel and a reflux condenser are placed 144 gms. (1 mole) of β-naphthol and 400 ml. of glacial acetic acid. Through the dropping funnel is then added a solution of 320 gms. (2 moles) of bromine in 100 ml. of acetic acid. The flask is shaken gently during the addition, which requires 15–30 minutes. The β-naphthol dissolves during this period, and heat is evolved; the mixture is cooled somewhat towards the end of the addition to avoid excessive loss of hydrogen bromide. One hundred milliliters of water is then added, and the mixture is heated to boiling. It is then cooled to 100° C., 25 gms. of mossy tin is added, and boiling is continued until the metal is dissolved. A second portion of 25 gms. of tin is then added and dissolved by boiling, and finally a third portion of 100 gms. (a total of 150 gms., 1.27 gram atoms) of tin is introduced. The mixture is boiled for 3 hours, cooled to 50° C., and filtered with suction. The crystalline tin salts which are thus removed are washed on the funnel with 100 ml. of cold acetic acid, the washings being added to the main portion of the filtrate.

This filtrate is stirred into 3 l. of cold water; the 6-bromo-2-naphthol which is precipitated is filtered with suction, removed from the funnel, and washed by stirring with 1 l. of cold water. After filtering again and drying at 100° C. there is obtained 214–223 gms. (96–100%) of 6-bromo-2-naphthol. This crude product, which is pink and melts at 123°–127° C., contains some tin but is pure enough for most purposes.

A white product is obtained by vacuum distillation followed by crystallization of the crude product. Twenty-five grams of the crude substance on distillation gives 20 to 24 gms. of distillate boiling at 200°–205° C./20 mm., and when this is crystallized from a mixture of 75 ml. of acetic acid and 150 ml. of water, it gives 17.5 to 22.5 gms. of 6-bromo-2-naphthol which melts at 127°–129° C.

EXAMPLE 2

Dissolved in 40 ml. of methanol are 8.52 gms. of 6-bromo-2-naphthol (0.0377 moles), 4.50 gms. of triethylamine, and 0.62 gms. of Pd(PPh$_3$)$_2$(OAc)$_2$ [bis-(triphenyl phosphine) palladous acetate]. The reaction mixture is then heated to a temperature maintained in the range of 109°–110° C. under a carbon monoxide atmosphere at a total pressure 920–990 psig for 72.5 hours. Carbon monoxide consumption is 0.046 moles.

The crude reaction mixture is filtered, dissolved in diethyl ether, and then washed with water, 10% HCl solution, and saturated sodium bicarbonate. The ether solution is then dried and stripped to recover a white solid residue. The white solid residue is washed with 125 ml. of 10% ether in petroleum ether and then dissolved in boiling diethyl ether. Petroleum ether is added hereto to precipitate 2.21 gms. of a white solid. The mother liquor is stripped, and 0.68 gms. of product is obtained by recrystallization of the residue from ethyl acetate. The total yield of product (the methyl ester of 6-hydroxy-2-naphthoic acid, namely, methyl 2-hydroxy-6-naphthoate) is 2.89 gms., 37%. The product is characterized by IR, NMR, $^{13}$C NMR, and mass spectrometry.

EXAMPLE 3

A solution of 8.61 gms. 6-bromo-2-naphthol (0.0386 moles), 0.62 gms. Pd(PPh$_3$)$_2$(OAC)$_2$[bis-(triphenyl phosphine) palladous acetate] (0.830 moles), 4.50 gms. triethylamine (0.044 moles), and 40 ml. methanol is heated to about 106°–107° C. under a carbon monoxide atmosphere at a total pressure of about 1000 psig in a 300 cc. autoclave reactor. After 15 hours, the pressure is 940 psig with a CO gas consumption of 0.042 moles. The pressure is then kept constant for another 6 hours.

The reactor is cooled and the resulting slurry is filtered, dissolved in diethyl ether, and then shaken with water, 20% hydrochloric acid solution, and saturated sodium bicarbonate. The resulting organic solution is dried with anhydrous MgSO$_4$, filtered, diluted with petroleum ether, and concentrated to about 10 ml. to thereby give a white precipitate, which after filtration and rinsing with diethyl ether/petroleum ether weighs 3.61 gms., representing a crude yield of 46%.

Upon recrystallization of the crude white solid from benzene, 1.835 gms. of methyl 6-hydroxy-2-naphthoate is obtained. Concentration of the benzene mother liquor gives an additional 0.766 gms. of product. The total yield of isolated methyl 6-hydroxy-2-naphthoate is 2.60 gms., 33%.

EXAMPLE 4

6-bromo-2-naphthol is obtained according to the procedure of Example 1. A solution of acetic anhydride, sodium acetate, and the 6-bromo-2-naphthol in toluene is then refluxed for about 2 ½ hours. Crude 2-acetoxy-6-bromonaphthalene is isolated therefrom by stripping the solvent from the organic layer after washing with water. The acetoxy compound is then purified by recrystallization from n-butanol.

10.0 gms. of the 2-acetoxy-6-bromonaphthalene (0.0377 moles), 4.50 gms. of triethylamine, and 0.60 gms. of Pd(PPh$_3$)$_2$(OAc)$_2$ are combined with 40 ml. of methanol in a 300 cc. autoclave reactor. The resulting mixture is heated to a temperature maintained in the range of 102°–109° C. under a carbon monoxide atmosphere at a total pressure of 590 psig for 3.5 hours. The pressure of carbon monoxide is then increased and maintained in the range of 950–1000 psig for an additional 68.5 hours. Carbon monoxide consumption upon completion of the reaction is about 0.033 moles.

The resulting solution is filtered, dissolved in 150 ml. of diethyl ether, and washed with water, 20% HCl solution, and saturated sodium bicarbonate. The organic layer is then dried with MgSO$_4$, mixed with an equal volume of hexane, and concentrated to 5–10 ml. An additional 10 ml. of hexane is added thereto and the obtained white solid crystals are filtered and rinsed with hexane. The product yield of methyl 2-hydroxy-6-naphthoate is 3.94 gms., 52%.

COMPARATIVE EXAMPLE 1

The comparative example illustrates the effect of conducting the carbonylation of a hydroxy aromatic halide, 6-bromo-2-naphthol, in the absence of a reactive alcohol solvent.

A solution comprising 16.1 gm. of 6-bromo-2-naphthol (0.072 mole), 1.53 gm. of tetrabutyl ammonium iodide (0.0014 mole), 1.54 gm. of triphenylphosphine (0.006 mole), 0.52 gm. of bis(benzonitrile) palladous chloride (0.0014 mole), and 50 ml. of xylene is mixed in an autoclave with 60 ml. of a 25% aqueous NaOH solution. This mixture is stirred at 130° C. under a carbon monoxide atmosphere for 21 hours. The pressure in the autoclave is maintained in the range of 260–500 psig.

A crude black product is isolated by separating the organic and aqueous layers after the addition of an additional 50 ml. xylene and 50 ml. H$_2$O to the reaction mixture and then acidifying the aqueous layer. The crude black product is recrystallized from water to give 0.19 gms. (0.0010 mole) of 6-hydroxy-2-naphthoic acid, melting point 235°–238° C., which is further characterized by IR and $^{13}$CNMR. The total yield of 6-hydroxy-2-naphthoic acid is only 1.4%.

The high yield, i.e., 33% and above, obtained in Examples 2-4 wherein the carbonylation reaction is conducted in an alcohol solvent illustrates the advantages of the instant process with respect to carbonylating hydroxy aromatic halides, and more particularly, with respect to synthesizing 6-hydroxy-2-naphthoic acid or its corresponding ester via β-naphthol as shown by Examples 1 and 2-4, when compared to the 1.4% yield obtained in Comparative Example 1 wherein the reaction is not run in the presence of an alcohol solvent.

Although the invention has been described with preferred embodiments, it is to be understood that variations and modifications may be resorted to as will be apparent to those skilled in the art. Such variations and modifications are to be considered within the purview of the scope of the claims appended hereto.

What is claimed:

1. A process for preparing the ester of a hydroxy aromatic carboxylic acid which comprises reacting a hydroxy aromatic halide with carbon monoxide in the presence of (i) a reactive alcohol solvent wherein said alcohol has from 1 to about 8 carbons, and (ii) a catalytic amount of a Group VIII catalyst, under carbonylation reaction conditions sufficient to produce the corresponding hydroxy ester of said hydroxy aromatic carboxylic acid.

2. The process of claim 1 wherein said reaction is conducted in the presence of a weak base.

3. The process of claim 1 wherein said hydroxy aromatic halide is selected from the group consisting of a halogenated naphthol and a halogenated phenol.

4. The process of claim 3 wherein the halogen is bromine.

5. The process of claim 4 wherein the hydroxy aromatic halide is 6-bromo-2-naphthol.

6. The process of claim 1 wherein said alcohol is methanol.

7. The process of claim 6 wherein the weight ratio of alcohol solvent to hydroxy aromatic halide is in the range from about 0.5 to about 100.

8. The process of claim 7 wherein said weight ratio is in the range from about 1 to about 10.

9. The process of claim 8 wherein said weight ratio is in the range from about 3 to about 8.

10. The process of claim 1 wherein said Group VIII catalyst is selected from the group consisting of a palladium, platinum, ruthenium, rhodium, osmium and indium catalyst.

11. The process of claim 10 wherein said catalyst is a palladium catalyst.

12. The process of claim 11 wherein said catalyst comprises bis(triphenyl phosphine) palladous acetate.

13. The process of claim 1 wherein a temperature in the range of about 20° C. to about 250° C. is employed in said reaction.

14. The process of claim 13 wherein said reaction temperature is in the range of about 90° C. to about 110° C.

15. The process of claim 1 wherein the process further comprises acidifying the hydroxy ester product to obtain the corresponding hydroxy acid.

16. The process of claim 2 wherein said weak base is a tertiary amine.

17. A process for preparing an ester derivative of 6-hydroxy-2-naphthoic acid from β-naphthol, which process comprises (i) reacting β-naphthol with bromine under bromination reaction conditions sufficient to yield 1,6-di-bromo-2-naphthol (ii) reacting said 1,6-di-bromo-2-naphthol with HBr in the presence of metallic tin and recovering the hydroxy aromatic halide product, (iii) carbonylating said product of (ii) with carbon monoxide in the presence of a reactive alcohol solvent, wherein said alcohol has from 1 to about 8 carbons, and a catalytic amount of a Group VIII catalyst under carbonylation reaction conditions sufficient to produce the ester of 6-hydroxy-2-naphthoic acid.

18. The process of claim 17 wherein the product of (ii) that is carbonylated is first acetylated by reacting said product with an acetylation agent under conditions sufficient to acetylate the hydroxy group of said product.

19. The process of claim 17 wherein said alcohol is methanol.

20. The process of claim 17 wherein said product of (ii) is carbonylated with carbon monoxide in the presence of triethylamine, methanol, and bis-(triphenyl phosphine) palladous acetate at a temperature in the range of about 90°-110° C. and under a carbon monoxide pressure maintained in the range of about 300-1000 psig.

21. The process of claim 18 wherein said acetylated product is carbonylated with carbon monoxide in the presence of triethylamine, methanol and bis-(triphenyl phosphine) palladous acetate at a temperature in the range of about 90°-110° C. and under a carbon monoxide pressure of about 300-1000 psig.

22. A process for preparing the ester of a hydroxy aromatic carboxylic acid which comprises reacting a hydroxy aromatic halide with carbon monoxide in the presence of
  (i) methanol, and
  (ii) a palladium catalyst, at a temperature in the range of about 90°-110° C. and at a total pressure maintained in the range of about 300-1000 psig.

23. The process of claim 22 wherein said hydroxy aromatic halide is 6-bromo-2-naphthol.

24. The process of claim 1 or 17 wherein the reactive alcohol solvent is a straight chain alcohol.

25. The process of claim 1 or 17 wherein the reactive alcohol solvent contains from 1 to about 4 carbon atoms.

26. The process of claim 1, wherein the reaction is conducted at a temperature in the range of from about 20° C. to about 250° C. and a pressure in the range of from about 100 to about 1500 psig, wherein the weight ratio of alcohol solvent to hydroxy aromatic halide is in the range of from about 0.5 to about 100, and wherein the amount of catalyst employed is in the range of from about 0.001 to about 20 mole percent based upon the amount of hydroxy aromatic halide employed.

27. The process of claim 1, 17, 22 or 26, wherein the ester product is obtained in a yield of at least 30 percent.

* * * * *